United States Patent [19]

Kishimoto et al.

[11] Patent Number: 4,942,159
[45] Date of Patent: Jul. 17, 1990

[54] CEPHEM COMPOUNDS, THEIR PRODUCTION AND USE

[75] Inventors: Shoji Kishimoto, Hyogo; Kiminori Tomimatsu; Akio Miyake, both of Osaka, all of Japan

[73] Assignee: Takeda Chemical Industries, Ltd., Osaka, Japan

[21] Appl. No.: 235,566

[22] Filed: Aug. 24, 1988

[30] Foreign Application Priority Data

Aug. 25, 1987 [JP] Japan .................. 62-212567

[51] Int. Cl.$^5$ .................. C07D 501/46; A61K 31/545
[52] U.S. Cl. .................... 514/202; 540/222
[58] Field of Search ................ 540/222; 514/202

[56] References Cited

U.S. PATENT DOCUMENTS 4,401,668  8/1983  Lunn .................... 540/222

FOREIGN PATENT DOCUMENTS 8605183  9/1986  PCT Int'l Appl. .

Primary Examiner—Anton H. Sutto
Assistant Examiner—C. L. Cseh
Attorney, Agent, or Firm—Wegner & Bretschneider

[57] ABSTRACT

Novel cephem compounds of the general formula:

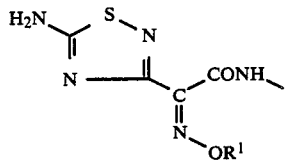
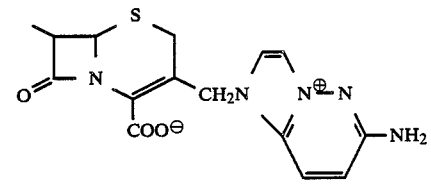

wherein $R^1$ is a lower alkyl group, and salts and esters thereof, showing excellent and balanced antibacterial activity against a broad spectrum of bacteria, especially by rectal administration, and their production and use as antimicrobial agents are described.

8 Claims, No Drawings

CEPHEM COMPOUNDS, THEIR PRODUCTION AND USE

The present invention relates to a novel class of cephem compounds and salts and esters thereof which have very desirable antibacterial activity. The cephem compounds and salts and esters thereof according to the invention are of value as antibacterial agents.

Cephem compounds having an imidazo[1,2-b]pyridazinium-1-yl group in the 3-position of a cephem ring have already been synthesized but the present cephem compounds having an amino group in the 6-position of the imidazo[1,2-b]pyridazine ring, or salts or esters thereof, have not been synthesized and, for that matter, their specifically excellent antibacterial properties are not known.

Cephem antibiotics are used widely in the treatment of various diseases caused by pathogenic bacteria in man and animals and are particularly of great use, for example, in the treatment of diseases caused by bacteria resistant to penicillin antibiotics and in the treatment of patients with hypersensitivity to penicillin antibiotics. In such cases, a cephem antibiotic active against both gram-positive and gram-negative bacteria particularly is desired and for this reason, cephem antibiotics having extended antibacterial spectra have been subjects of intensive research. Actually, several so-called third generation cephalosporin antibiotics are already available commercially. However, none of these antibiotics are fully satisfactory and there remains to be found a compound having high activity against both *Staphylococcus aureus* and *Pseudomonas aeruginosa* or a compound showing high activity against highly β-lactamase-producing clinically isolated strains such as those of *Citrobacter freundii* and *Enterobacter cloacae*. Therefore, there has been a demand for a highly antibacterial compound which may be used broadly against gram-positive and gram-negative bacteria inclusive of such clinically isolated strains.

The present invention relates to a cephem compound of the general formula:

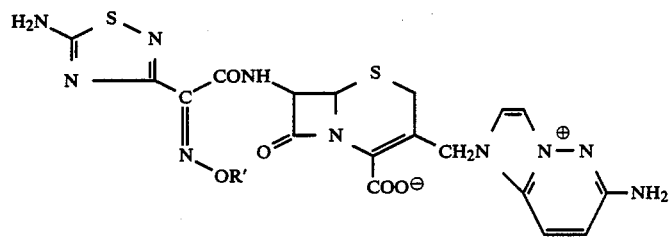

wherein $R^1$ is a lower alkyl group or a salt or ester thereof and to an antibacterial composition containing said cephem compound (I) or salt or ester thereof and to a process for the preparation thereof.

The cephem compound (I) or salt or ester thereof is structurally characterized in that a group of the formula:

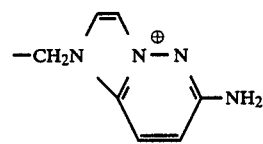

exists in the 3-position of the cephem ring, and by virtue of the specific combination of this 3-substituent group with the 7-acyl group, exhibits balanced antibacterial activity against a broad spectrum of bacteria covering both gram-positive and gram-negative bacteria inclusive of various clinical strains (such as clinical strains of *Citrobacter freundii* and *Enterobacter cloacae*.

The present invention provides a cephem compound (I) or a salt or ester thereof, which has such excellent characteristics.

Referring to the above general formula, $R^1$ is a lower alkyl group, which is a branched or straight-chain alkyl group containing 1 to 4 carbon atoms, such as methyl, ethyl, n-propyl, i-propyl, n-butyl, i-butyl, sec-butyl, t-butyl and so on. Particularly preferred are methyl and ethyl.

Referring to general formula (I), the positive charge (+) of the 3-substituent group is shown on the nitrogen atom in the 4-position of the imidazo[1,2-b]pyridazine ring for convenience's sake but it may be present on the nitrogen atom in the 1-position thereof or be ubiquitously present on the imidazole ring or even on the condensed ring system as a whole. Therefore, the moiety

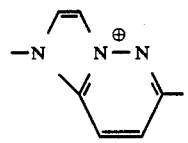

(I)

in the compound of general formula (I) may also be written, for example as follows.

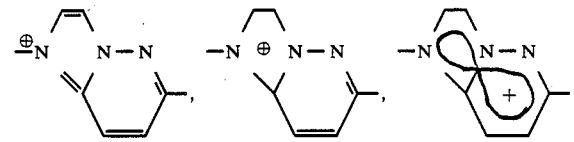

The position of this positive charge may be transitory and is dependent on the environment in which the cephem compound (I) or salt or ester thereof is present (whether it occurs as a solid or in solution), kind of solvent, pH, temperature and so on, and the present invention covers all the cases in which the positive charge is localized on a nitrogen atom or delocalized (ubiquitously present) on the imidazole ring or the condensed ring system.

The cephem compound (I) or salt or ester thereof is a syn-isomer ([Z]-isomer).

The salt of cephem compound (I) is preferably a pharmaceutically acceptacle salt. As examples of such pharmaceutically acceptable salt, there may be mentioned the corresponding addition salt with an inorganic acid or an organic acid. Inorganic acids which may give such inorganic acid addition salt include hydrochloric acid, hydrobromic acid, sulfuric acid, nitric acid, phosphoric acid and so on. Organic acids which may give said organic acid addition salt include p-toluenesulfonic acid, methanesulfonic acid, formic acid, trifluoroacetic acid, maleic acid, fumaric acid and so on. The acid addition salt (i.e. inorganic acid addition salt or organic acid addition salt) means any acid addition salt that may be formed with the basic moiety of cephem compound (I). This acid addition salt includes, for example, the salt formed as one molecule of the acid is added to the inner salt moiety of cephem compound (I), between the carboxylate moiety (COO⊖) in the 4-position and the moiety

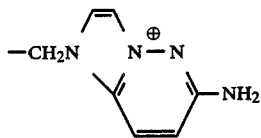

3-position, wherein the 4-position is a free carboxyl group (COOH) and the 3-position is

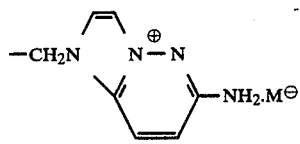

wherein M⊖ is an anion formed on removal of a proton (H⊕) from the inorganic or organic acid used, such as chloride ion, bromide ion, sulfate ion, p-toluenesulfonate ion, methanesulfonate ion, trifluoroacetate ion or the like. Preferred salts of cephem compound (I) are inorganic addition salts and most desirably hydrochloride or sulfate.

The ester of cephem compound (I) is preferably a pharmaceutically acceptable ester which means an ester derivable by esterifying the carboxyl group contained in the molecule, and includes an ester usable as a synthetic intermediate and a bioavailably unstable non-toxic ester. As examples of such esters usable as synthetic intermediates, there may be mentioned $C_{1-6}$ alkyl ester which may be substituted (e.g. methyl, ethyl, n-propyl, isopropyl, n-butyl, isobutyl, sec-butyl, tert-butyl, n-pentyl, n-hexyl, benzyloxymethyl, 2-methylsulfonylethyl, 2-trimethylsilylethyl, 2,2,2-trichloroethyl, 2-iodoethyl, acetylmethyl, p-nitrobenzoylmethyl, p-mesylbenzoylmethyl, phthalimidomethyl, succinimidomethyl, benzenesulfonylmethyl, phenylthiomethyl, dimethylaminoethyl, pyridine-1-oxido-2-methyl, methylsulfinylmethyl, or 2-cyano-1,1-dimethylethyl ester), $C_{2-6}$ alkenyl ester (e.g. vinyl, allyl, 1-propenyl, isopropenyl, 1-butenyl, 2-butenyl, 3-butenyl, methallyl, 1,1-dimethylallyl or 3-methyl-3-butenyl ester), $C_{3-10}$ cycloalkyl ester (e.g. cyclopropyl, cyclobutyl, cyclopentyl, cyclohexyl, cycloheptyl, norbornyl or adamantyl ester), $C_{3-10}$ cycloalkyl $C_{1-6}$ alkyl ester (e.g. cyclopropylmethyl, cyclopentylmethyl or cyclohexylmethyl ester), $C_{6-10}$ aryl ester which may be substituted (e.g. phenyl, α-naphthyl, β-naphthyl, biphenylyl, p-nitrophenyl or p-chlorophenyl ester), $C_{7-12}$ aralkyl ester which may be substituted (e.g. benzyl, 1-phenylethyl, 2-phenylethyl, phenylpropyl, naphthylmethyl, p-nitrobenzyl, p-methoxybenzyl, 1-indanyl, phenacyl or 3,5-di-tert-butyl-4-hydroxybenzyl ester), di-$C_{6-10}$ aryl-methyl ester (e.g. benzhydryl or bis(p-methoxyphenyl)methyl ester), tri-$C_{6-10}$ aryl-methyl ester (e.g. trityl ester) and substituted silyl ester (e.g. trimethylsilyl, tert-butyldimethylsilyl or —Si(CH$_3$)$_2$CH$_2$CH$_2$Si(CH$_3$)$_2$-ester). As examples of such bioavailably unstable and non-toxic esters, i.e. those which have been confirmed as employable in the fields of penicillin and cephalosporin, there may be mentioned $C_{2-6}$ alkanoyloxy-$C_{1-6}$ alkyl ester, 1-($C_{1-6}$ alkoxy)$C_{1-6}$ alkyl ester or 1-($C_{1-6}$ alkylthio)$C_{1-6}$ alkyl ester. The $C_{2-6}$ alkanoyloxy-$C_{1-6}$ alkyl ester is exemplified by acetoxymethyl ester, 1-acetoxyethyl ester, 1-acetoxybutyl ester, 2-acetoxyethyl ester, propionyloxymethyl ester, pivaloyloxymethyl ester. The 1-($C_{1-6}$ alkoxy)$C_{1-6}$ alkyl ester is exemplified by methoxymethyl ester, ethoxymethyl ester, isopropoxymethyl ester, 1-methoxyethyl ester or 1-ethoxyethyl ester. The 1-($C_{1-6}$ alkylthio)$C_{1-6}$ alkyl ester is exemplified by methylthiomethyl ester or ethylthiomethyl ester. The present invention includes, besides the above-mentioned esters, pharmaceutically acceptable compounds which are convertible in vivo to the compound [I]. The above-mentioned esters usable as synthetic intermediates and bioavailably unstable non-toxic esters mean esters at the 4-position. When esters are formed in the carboxyl group at the 4-position, usually an intramolecular salt of

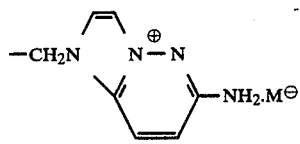

wherein M⊖ has the same meaning as defined above, is formed at the 3-position.

The following is a partial of cephem compounds (I) of the invention which are possessed of the aforementioned characteristics.

(1) 7β-[2-(5-Amino-1,2,4-thiadiazol-3-yl)-(Z)-2-methoxyiminoacetamido]-3-[(6-aminoimidazo[1,2-b]pyridazinium-1-yl)methyl]-3-cephem-4-carboxylate (2) 7β-[2-(5-Amino-1,2,4-thiadiazol-3-yl)-(Z)-2-ethoxyiminoacetamido]-3-[(6-aminoimidazo[1,2-b]pyridazinium-1-yl)methyl]-3-cephem-4-carboxylate The cephem compound (I) or salt or ester thereof is an invaluable antibiotic showing marked antibacterial activity against gram-positive and gram-negative bacteria inclusive of clinically isolated strains and can be used as drugs for man and domestic animals. Thus, the compound can be safely used as an antibacterial agent (preferably suppository), for the treatment or prevention of infections caused by various bacteria.

Furthermore, the cephem compound (I) or salt or ester thereof according to the invention can be incorporated in animal feeds for the purpose of preventing spoilage of the feedstuffs. Moreover, it can be used as a bactericide for destroying harmful bacteria on medical or dental equipment and devices or as an industrial bactericide for arresting growth of noxious bacteria in water-based paints, paper mill white water and so on.

The cephem compound (I) or salt or ester thereof of the invention can be used either alone or in combination with other active agents and, if necessary, can be formulated with various additives such as a neutralizing agent, a stabilizer, a dispersing agent, etc. to provide such dosage forms as capsules, tablets, powders, solution, suspension, elixer, etc. in the usual manner. Such compositions can be administered parenterally (for example, by intravenous or intramuscular injection or rectal administration) or orally.

The composition for injection can be provided in unit dosage forms, such as ampules or preservative-containing vessels. The composition may also be a suspension, solution or emulsion in an oily or aqueous vehicle and may contain the usual auxiliary agents such as suspending agents, neutralizing agents, stabilizers and/or dispersing agents in appropriate amounts. The cephem compound (I) or salt or ester thereof may be provided as granules or powders which are extemporaneously dissolved in an appropriate vehicle such as sterilized pyrogen-free water or an aqueous solution of sodium hydrogen carbonate or sodium carbonate.

The cephem compound (I) or salt or ester thereof can be processed into tablets, capsules, granules or powders for oral administration by mixing it with a binder such as syrup, gum arabic, gelatin, sorbitol, gum tragacanth, polyvinylpyrrolidone, etc., a filler such as lactose and other sugars, corn starch, calcium phosphate, sorbitol, glycine, etc., a lubricating agent such as magnesium stearate, talc, polyethylene glycol, silica, etc., a disintegrating agent such as potato starch etc. or a wetting agent such as sodium laurylsulfate etc. and subjecting the mixture to the conventional manufacturing procedure for the corresponding dosage form. The tablets, granules, etc. can be film-coated by the established pharmaceutical procedure. The composition for oral administration can be provided in the form of a liquid preparation such as an aqueous or oily suspension, solution, emulsion, syrup or an elixer.

The composition for rectal administration of the present invention is produced, according to the per se conventional manner, by mixing a suppository base, additive(s) and the cephem compound (I) or salt or ester thereof, and shaping the resulting mass into fatty solid suppositories, semi-solid ointment-like suppositories, capsule suppositories consisting of the liquid composition filled in soft capsules, etc. A ratio of the cephem compound (I) or salt or ester thereof relative to the whole composition is generally selected from a range of approximately 0.5 to 50, preferably 5 to 30 weight %, but not limited thereto. The ratio varies depending on the compounds employed, weight of the composition, etc. For purposes of enhancing absorption or controlling the ratio of absorption, etc. of the cephem compound (I) or salt or ester thereof in the present invention, any other nonionic surfactant such as polyoxyethylene fatty acid ester and a polyoxyethylene higher alcohol ether may be further incorporated in the composition, or alternatively an anionic surfactant can be used. In addition, a variety of salts or stabilizers can also be incorporated and added in order to increase the solubility or stability of the compound (I) or salt or ester thereof. A dispersing agent, antiseptic agent, polyoxyethylene cholesterol ether or polyethylene hydrogenated cholesterol ether as described in EP-A-33241, etc., besides, can be added, if it is considered necessary.

In these compositions, the conventional antioxidants, preservatives, lubricating agents, thickeners and corrigents may be incorporated in the conventional manner. Furthermore, compositions showing a further extended antibacterial spectrum can be provided by adding one or more other active ingredients (such as other $\beta$-lactam antibiotics) to the above-mentioned compositions.

For domestic animals, the composition of the invention can be used as intramammary composition prepared using a pharmaceutical base adapted for sustained or fast release of the active substance.

The cephem compound (I) or salt or ester thereof according to the present invention can be used as a prophylactic/therapeutic agent for bacterial infections in man and domestic animals. Thus, it may be indicated broadly in respiratory tract infections, urinary tract infections, supprative diseases, biliary tract infections, intestinal infections, gynecological and obstetric infections, and surgical infections. The daily dosage of the cephem compound (I) or salt or ester thereof depends on the patient's condition and body weight, the administration schedule and so on. Taking the parenteral route as an example, the composition of the invention can be administered in a daily dose of about 0.5 to 80 mg as active ingredient (cephem compound (I) or salt or ester thereof) per kilogram body weight for adults and preferably about 1 to 20 mg on the same basis. The above dosage is preferably administered by intraveous injection, drip infusion or rectal administration in 2 to 4 divided doses. The preferred daily dosage for oral administration is about 5 to 100 mg as active ingredient (cephem compound (I) or salt or ester thereof) per kg body weight for adults, to be given in 1 to 3 divided doses.

In addition, the cephem compound (I) or salt or ester thereof is an ideal antibacterial agent which shows a very satisfactory distribution profile in the body, is substantially free of side effects, and exhibits excellent therapeutic and prophylactic effects against the aforementioned various infections in a brief time after administration.

The cephem compound (I) or salt or ester thereof can be produced by the processes known per se (for example, the processes described in EP-A-203271 and EP-A-160252. Alternatively, it can be produced by the following production processes 1 to 3.

Production process 1

The cephem compound (I) or salt or ester thereof can be produced by reacting a compound of the general formula:

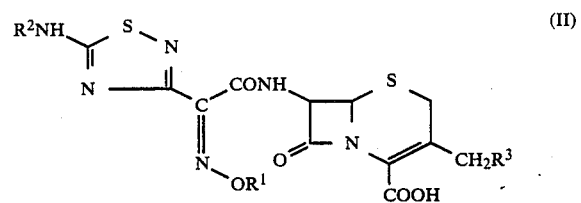

(II)

wherein R[1] has the same meaning as defined hereinbefore; R[2] is a hydrogen atom or an amino-protecting group; R[3] is a hydroxyl group, an acyloxy group, a carbamoyloxy group, a substituted carbamoyloxy group or a halogen atom, or a salt or ester thereof with a compound of the general formula:

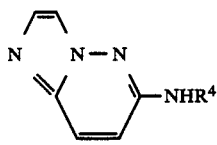
(III)

wherein R[4] is a hydrogen atom or an amino-protecting group or a salt thereof and, if required, in an optional order, eliminating the protective group or groups, converting the resulting salt or ester to the corresponding carboxylate or free base or the resulting carboxylate or free base to a pharmaceutically acceptable salt or ester.

Referring to the above general formulas, the acyloxy group of R[3] includes, among others, formyloxy, acetoxy, propionyloxy, butyryloxy, valeryloxy, pivaloyloxy, chloroacetoxy, dichloroacetoxy, trichloroacetoxy, 3-oxobutyryloxy, 4-chloro-3-oxobutyryloxy, 3-carboxypropionyloxy, 4-carboxybutyryloxy, 3-ethoxycarbamoylpropionyloxy, benzoyloxy, naphthoyloxy, p-methylbenzoyloxy, p-methoxybenzoyloxy, p-chlorobenzoyloxy, o-carboxybenzoyloxy, o-(ethoxycarbonylcarbamoyl)benzoyloxy, o-(ethoxycarbonylsulfamoyl)benzoyloxy, phenylacetyloxy, p-methylphenylacetyloxy, p-methoxyphenylacetyloxy, p-chlorophenylacetyloxy, 2,2-diphenylacetyloxy, thienylcarbonyloxy, furylcarbonyloxy, thiazolylacetyloxy, thienylacetyloxy, furylacetyloxy and so on. The substituted carbamoyloxy group of R[3] includes, among others, N-methylcarbamoyloxy, N,N'-dimethylcarbamoyloxy, N-ethylcarbamoyloxy, N-phenylcarbamoyloxy and so on. The halogen of R[3] includes chlorine, bromine and iodine, among others.

The amino-protecting group, represented by R[2] and R[4] hereinabove, can be selected from among various amino-protecting groups which are routinely used in the field of β-lactam and peptide chemistry and includes, as preferred species, formyl, monochloroacetyl, phthaloyl, tert-butoxycarbonyl, benzyloxycarbonyl, p-methoxybenzyloxycarbonyl, p-nitrobenzyloxycarbonyl, 2-trimethylsilylethoxycarbonyl, 2,2,2-trichloroethoxycarbonyl, trityl, o-nitrophenylthio and so on.

The salt of compound (II) is the salt with a base which is able to promote the reaction, to neutralize the acid produced by the reaction or to increase the solubility of the starting compound. As examples of such base, there may be mentioned tertiary amines such as triethylamine, tri-n-butylamine, diisopropylethylamine, etc. and hydrogen carbonates of alkali metals such as sodium hydrogen carbonate, potassium hydrogen carbonate and so on. For the purposes mentioned just above, such a base can be added together with compound (II) to the reaction system and generally its level of addition is preferably about 1 to 5 moles per mole of compound (II). As the ester of compound (II), there may be used the same ester as mentioned in the cephem compound (I). As examples of said salt of compound (III), there may be mentioned addition salts with inorganic acids such as hydrochloric acid, hydrobromic acid, sulfuric acid, nitric acid, phosphoric acid, and addition salts with organic acids such as formic acid, acetic acid, trifluoroacetic acid, methanesulfonic acid, p-toluenesulfonic acid and so on.

(1): Where R[3] is a hydroxy group

In this reaction, the compound (III) or salt thereof is used in a proportion of about 1 to 10 moles, preferably about 1 to 5 moles, per mole of the compound (II) or salt or ester thereof. This reaction is generally conducted in an organic solvent which does not interfere with its progress. As examples of the solvent which does not interfere with the reaction, there may be mentioned various amides such as formamide, dimethylformamide, dimethylacetamide, etc.; halogenated hydrocarbons such as dichloromethane, chloroform, 1,2-dichloroethane, etc.; ethers such as diethyl ether, tetrahydrofuran, dioxane, etc.; esters such as methyl acetate, ethyl acetate, isobutyl acetate, methyl propionate, etc.; nitriles such as acetonitrile, propionitrile, etc.; nitro compounds such as nitromethane, nitroethane, etc.; ketones such as acetone, methyl ethyl ketone, etc.; and aromatic hydrocarbons such as benzene, toluene and so on. These solvents can be used ether singly or as an appropriate mixture of two or more species. Particularly preferred are dichloromethane, tetrahydrofuran, acetonitrile, formamide, dimethylformamide, etc., a mixture of dimethylformamide and acetonitrile, a mixture of dichloromethane and acetonitrile and a mixture of dichloromethane and tetrahydrofuran and so on.

For the purpose of promoting this reaction, a cyclic phosphorus compound as described in U.S. Pat. No. 4,642,365 or a phosphorous ester can be employed. For example, a cyclic phosphorus compound of the general formula:

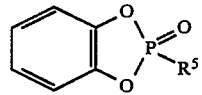
(IV)

wherein R[5] is a phenyl group or a lower alkoxy group, can be employed. Referring to this general formula (IV), the lower alkoxy group of R[5] is an alkoxy group containing 1 to 4 carbon atoms, such as methoxy, ethoxy, propoxy, isobutoxy and so on. Among such cyclic phosphorus compounds (IV), methyl o-phenylenephosphate, ethyl o-phenylenephosphate, 2-phenyl-2-oxo-1,3,2-benzodioxaphosphor, etc. are preferable. The compound (IV) is used in a proportion of about 1 to 10 moles, preferably about 1 to 6 moles, per mole of the compound (II) or salt or ester thereof. When a compound (IV) is used in the reaction, the compound (II) or salt or ester thereof, the compound (III) or salt thereof and the compound (IV) are reacted in an organic solvent such as mentioned above. Thus, the compound (II) or salt or ester, thereof is mixed with the compound (III) or salt thereof in said organic solvent and either the compound (IV) or a solution thereof in said organic solvent is then added. Or the compound (III) or salt thereof is mixed with the compound (IV) in said organic solvent and either the compound (II) or salt or ester thereof or a solution thereof in said organic solvent is then added.

The reaction temperature depends on the particular species and quantities of starting compound (II) or salt or ester thereof, compound (III) or salt thereof, said cyclic phosphorus compound (IV), organic solvent, base and so on but is generally about −80° C. to 60° C. The reaction time is about 1 minute to 24 hours.

(2): Where $R^3$ is an acyloxy group, a carbamoyloxy group or a substituted carbamoyloxy group The preferred solvent is water or a mixture of water with a water-miscible organic solvent. Preferred examples of such water-miscible organic solvent are acetone, methyl ethyl ketone, acetonitrile, etc.

The compound (III) or salt thereof is used in a proportion of generally about 1 to 5 moles and preferably about 1 to 3 moles per mole of the compound (II) or salt or ester thereof. This reaction is conducted in the temperature range of about 10° to 100° C. and preferably at about 30° to 80° C. The reaction time is generally about 30 minutes to 5 days and preferably about 1 to 5 hours. The reaction is preferably conducted at pH between 2 and 8, and more preferably in the neutral region, namely between pH 5 and 8. This reaction generally proceeds readily in the presence of about 2 to 30 equivalents of an iodide or a thiocyanic acid salt. As examples of such iodide, there may be mentioned sodium iodide, potassium iodide and so on. The thiocyanic acid salt may for example be sodium thiocyanate, potassium thiocyanate or the like. The progress of the reaction may also be rendered smooth by adding a surface active quaternary ammonium salt such as trimethylbenzylammonium bromide, triethylbenzylammonium bromide, triethylbenzylammonium hydroxide and so on.

(3): Where $R^3$ is a halogen atom

Preferred examples of the solvent are the solvents mentioned under (1) hereinbefore, such as ethers, esters, halogenated hydrocarbons, aromatic hydrocarbons, amides, ketones and nitriles, as well as water and alcohols such as methanol, ethanol, propanol and so on. The compound (III) or salt thereof is used in a proportion of generally about 1 to 5 moles and preferably about 1 to 3 moles per mole of the compound (II) or salt or ester thereof. This reaction is conducted in the temperature range of about 0° to 80° C. and preferably about 20° to 60° C. The reaction time is generally about 30 minutes to 15 hours and preferably about 1 to 5 hours. The reaction can be hastened by conducting it in the presence of a hydrogen halide acceptor. As examples of such hydrogen halide acceptor, there may be mentioned inorganic bases such as sodium carbonate, potassium carbonate, calcium carbonate, sodium hydrogen carbonate, etc., tertiary amines such as triethylamine, tri(n-propyl)amine, tri(n-butyl)amine, diisopropylethylamine, cyclohexyldimethylamine, pyridine, lutidine, γ-collidine, N,N-dimethylaniline, N-methylpiperidine, N-methylpyrrolidine, N-methylmorpholine, etc., and alkylene oxides such as propylene oxide, epichlorohydrin and so on. The compound (III) as such may be utilized as a hydrogen halide acceptor. In this case, compound (III) is used in a proportion of at least 2 moles per mole of the compound (II) or salt or ester thereof. The halogen of $R^3$ may be chlorine, bromine or iodine and is preferably iodine. The compound (II) in which $R^3$ is an iodine atom can be easily produced by the process described in EP-A-74268 or a process analogous thereto.

The reaction product can be isolated and purified by procedures known per se, such as solvent extraction, pH adjustment, redistribution, salting-out or fractional precipitation, crystallization, recrystallization and chromatography. Where the reaction product contains a protective group, the protective group may be eliminated, if necessary, to give the compound (I) or salt or ester thereof. For removal of such protective group, various known procedures such as a procedure using an acid, a base or hydrazine, a reductive deprotection reaction, a procedure using sodium N-methyldithiocarbamate, and so on can be selectively employed. Thus, the amino-protecting group can be easily removed by a known process or a process analogous thereto. Depending on the type of protective group, the process using an acid, the process using a base or a reductive process can be selected and used. In the process using an acid, the acid may be an inorganic acid such as hydrochloric acid, sulfuric acid, phosphoric acid or the like, an organic acid such as formic acid, trifluoroacetic acid, propionic acid, benzenesulfonic acid, p-toluenesulfonic acid or the like, or an acidic ion exchange resin, although the optimum acid may be different with the type of protective group and other conditions. In the process using a base, inorganic bases such as the hydroxides or carbonates or alkali metals such as sodium, potassium, etc. or of alkaline earth metals such as calcium, magnesium, etc., organic bases such as metal alkoxides, organic amines, quaternary ammonium salts, etc. and basic ion exchange resins can be used, although the optimum base depends on the type of protective group and other conditions. Where the above process using an acid or a base is conducted in a solvent, the solvent is preferably a hydrophilic organic solvent, water or a mixture thereof in many instances. For reductive deprotection, the process using a metal such as tin or zinc or a metal compound such as chromium dichloride or chromium acetate in combination with an organic or inorganic acid such as acetic acid, propionic acid or hydrochloric acid or the catalytic reduction process using a metal catalyst can be employed, although the choice depends on the kind of protective group and other conditions. Examples of the catalyst used in such a catalytic reduction process include platinum catalysts such as platinum wire, platinum sponge, platinum black, platinum oxide, colloidal platinum, etc., palladium catalysts such as palladium sponge, palladium black, palladium oxide, palladium-on-barium sulfate, palladium-on-barium carbonate, palladium-on-carbon, palladium-on-silica gel, colloidal palladium, etc.; and nickel catalysts such as reduced nickel, nickel oxide, Urushibara nickel and so on. In the reductive deprotection process using a metal and an acid, a metal such as iron, chromium or the like and either an inorganic acid such as hydrochloric acid or an organic acid such as formic acid, acetic acid, propionic acid or the like can be employed. The reductive deprotection reaction is generally carried out in a solvent. Thus, in the catalytic reduction process, for instance, an alcohol such as methanol, ethanol, propanol, isopropyl alcohol or ethyl acetate is frequently used. In the process using a metal and an acid, water or acetone is commonly used as the solvent but where the acid is liquid, it can be used as the solvent as well. In all the process using an acid, the process using a base and the reductive deprotection process, the reaction is generally conducted under cooling to mild warming. Where the amino-protecting group is monochloroacetyl, it can be easily removed by using, for example, thiourea or sodium N-methyldithiocarbamate. All told, elimination of the amino-protecting group can be accomplished by a process known per se.

Production Process 2

The cephem compound (I) or salt or ester thereof can also be produced by reacting a compound of the general formula:

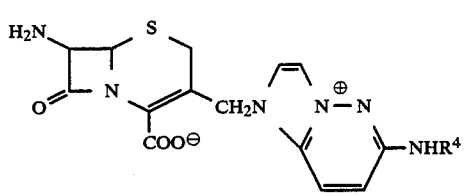

wherein $R^4$ has the same meaning as defined hereinbefore, or a salt or ester thereof with a compound of the general formula:

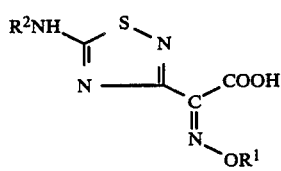

wherein $R^1$ and $R^2$ have the same meanings as defined hereinbefore, or a reactive derivative of the carboxyl function thereof and, if desired, in an optional order, eliminating the protective group or groups, converting the resulting salt or ester to the corresponding carboxylate or free base or the resulting carboxylate or free base to a pharmaceutically acceptable salt or ester.

As the salt of compound (V), there can be employed a salt with any of bases similar to those mentioned for the salt of compound (II) and such a base can be added together with the compound (V) to the reaction system. The level of addition of such base is generally about 1 to 10 moles and preferably about 1 to 5 moles per mole of compound (V). And, as the ester of compound (V), there can be employed the same ester as mentioned in the cephem compound (I).

The reactive derivatives of the carboxyl function of compound (VI) include, among others, acid halides, acid anhydrides, active amides, active esters, active thioesters, etc., all of which can be prepared by the known procedures. Specific examples of such reactive derivatives are as follows.

(1) Acid halides:
The corresponding acid chloride, acid bromide, etc.

(2) Acid anhydrides:
The corresponding mixed acid anhydride with a mono-lower alkylcarbonic acid, for instance.

(3) Active amides:
For example, the corresponding amides with pyrazole, imidazole, 4-substituted imidazoles, dimethylpyrazole, benzotriazole, etc.

(4) Active esters:
For example, the corresponding methoxymethyl ester, benzotriazole ester, 4-nitrophenyl ester, 2,4-dinitrophenyl ester, trichlorophenyl ester, pentachlorophenyl ester, etc. and esters with 1-hydroxy-1H-2-pyridone, N-hydroxysuccinimide, N-hydroxyphthalimide, etc.

(5) Active thioesters:
For example, the corresponding thioesters such as those with heterocyclethiols, e.g. 2-pyridylthiol, 2-benzothiazolylthiol, etc.

In this reaction, the compound (VI) or a reactive derivative of its carboxyl function is used in a proportion of at least 1 mole, preferably about 1 to 4 moles, per mole of the compound (V) or salt or ester thereof. This reaction is generally conducted in a solvent. Examples of the solvent mentioned just above include water; ketones such as acetone, etc.; ethers such as tetrahydrofuran, dioxane, etc.; nitriles such as acetonitrile, etc.; halogenated hydrocarbons such as dichloromethane, chloroform, 1,2-dichloroethane, etc.; esters such as ethyl acetate, etc.; and amides such as dimethylformamide, dimethylacetamide, and so on. These solvents can be used either singly or as an appropriate mixture of two or more species. Where compound (VI) is used in its free form, the reaction is preferably conducted in the presence of a condensing agent. Examples of such condensing agent include N,N'-dicyclohexylcarbodiimide, N-cyclohexyl-N'-morpholinoethylcarbodiimide, N-cyclohexyl-N'-(4-diethylaminocyclohexyl)carbodiimide, N-ethyl-N'-(3-dimethylaminopropyl)carbodiimide and so on. The reaction may also be conducted in the presence of a base such as an alkali metal carbonate, e.g. sodium carbonate, potassium carbonate, etc., or a tertiary amine, e.g. triethylamine, tri-n-butylamine, N-methylmorpholine, N-methylpiperidine, N,N-dimethylaniline, pyridine, picoline, lutidine and so on. These bases have the property to accelerate the reaction, neutralize the acid produced in the course of the reaction or increase the solubility of the starting compound and are generally used in a proportion of about 0.01 to 10 moles, preferably about 0.1 to 5 moles, per mole of the compound (V) or salt or ester thereof. The reaction temperature is not critical but generally the reaction is carried out at about $-30°$ C. to $50°$ C. in many instances. The reaction time may range from several minutes to tens of hours (e.g. 5 minutes to 30 hours). The reaction product can be isolated and purified by the conventional procedure as in Production Process 1. Where the product contains a protective group, it can be removed, if desired, by the conventional procedure, for example the deprotection processes described hereinbefore, to give the cephem compound (I) or salt or ester thereof.

Production Process 3

The cephem compound (I) or salt or ester thereof can also be produced by reacting a compound of the general formula:

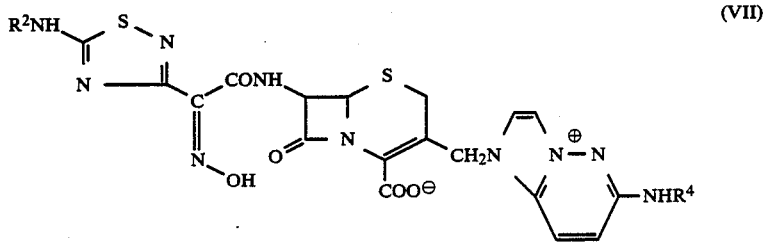

(VII)

wherein $R^2$ and $R^4$ have the same meanings as defined hereinbefore, or a salt or ester thereof with a compound of the general formula:

$$R^1OH \qquad\qquad (VIII)$$

wherein $R^1$ has the same meaning as defined hereinbefore or a reactive derivative thereof and, if desired, in an optional order, eliminating the protective group or groups, converting the resulting salt or ester to the carboxylate or free base or the resulting carboxylate or free base to a pharmaceutically acceptable salt or ester.

This reaction process comprises reacting a hydroxyimino compound (VII) or a salt or ester thereof with a compound (VIII) of the general formula $R^1OH$ or a reactive derivative thereof to give the cephem compound (I) or salt or ester thereof. As examples of the salt and ester of compound (VII), there may be mentioned acid addition salts and esters similar to those mentioned for the salt and ester of compound (I), respectively. The compound (VIII) is used either as it is or in the form of a reactive derivative. Such reactive derivative of (VIII) may be a derivative of $R^1OH$ containing a group which leaves with a hydrogen atom of hydroxyimino compound (VII), such as a compound of general formula $R^1Y$, diazoalkanes, dialkyl sulfates and so on. In the formula $R^1Y$, Y may for example be a halogen atom or a mono-substituted sulfonyloxy group. The halogen of Y may for example be chlorine, bromine or iodine. Examples of said mono-substituted sulfonyloxy group of Y include alkylsulfonyloxy groups such as methanesulfonyloxy, ethanesulfonyloxy, etc. and arylsulfonyloxy groups such as benzenesulfonyloxy, p-toluenesulfonyloxy and so on. Said diazoalkanes may be diazomethane, diazoethane or the like and said dialkyl sulfates may be dimethyl sulfate, diethyl sulfate or the like.

The compound (VII) or salt or ester thereof can be synthesized by the acylation reaction (using an acylating agent of $R^1=H$) described in Production Process 2 or the 3-substitution reaction (using a starting compound (II) of $R^1=H$ or a salt or ester thereof) described in Production Process 1.

(1) Where $R^1OH$ is used:

Using an appropriate dehydrating agent, the hydroxyimino compound (VII) or salt or ester thereof is reacted with Compound (VIII) to produce the cephem compound (I) or salt or ester thereof. As examples of the dehydrating agent that can be used for this purpose, there may be mentioned phosphorus oxychloride, thionyl chloride, dialkyl azodicarboxylates (usually in combination with a phosphine), N,N'-dicyclohexylcarbodiimide and so on. Preferred is diethyl azodicarboxylate in combination with triphenylphosphine. The reaction using diethyl azodicarboxylate in combination with triphenylphosphine is generally carried out in an anhydrous solvent, which may be selected from among the ethers and aromatic hydrocarbons mentioned hereinbefore. Based on one mole of the hydroxyimino compound (VII) or salt or ester thereof, each of the compound (VIII), diethyl azodicarboxylate and triphenylphosphine is used in a proportion of about 1 to 1.5 moles. The reaction temperature is about 0° C. to about 50° C. The reaction time is about 1 to 4 days.

(2) Where $R^1Y$ is used:

The reaction between $R^1Y$ and the hydroxyimino compound (VII) or salt or ester thereof can be conducted by the conventional etherization procedure and is carried out in a solvent. As the solvent, ethers, esters, halogenated hydrocarbons, aromatic hydrocarbons, amides, ketones, nitriles, alcohols and water, as well as mixtures thereof, which have been mentioned in Production Process 1 can be employed. Preferred is a mixture of water with a water-miscible solvent (such as aqueous methanol, aqueous ethanol, aqueous acetone, aqueous dimethyl sulfoxide, etc.). This reaction can be conducted smoothly in the presence of a base. As the base, various inorganic bases such as alkali metal salts, e.g. sodium carbonate, sodium hydrogen carbonate, potassium carbonate, etc., and alkali metal hydroxides, e.g. sodium hydroxide, potassium hydroxide, etc., can be employed. This reaction may also be carried out in a buffer solution at pH 7.5 to 8.5. The molar proportions of the reagent $R^1Y$ and said base per mole of the compound (VII) or salt or ester thereof are about 1 to 5 moles and about 1 to 10 moles, respectively, and preferably about 1 to 3 moles and about 1 to 5 moles, respectively. The reaction temperature is about −30° C. to about 100° C. and preferably about 0° to 80° C. The reaction time is about 10 minutes to 15 hours and preferably about 30 minutes to 5 hours.

(3) Where a diazoalkane is used:

The reaction is generally carried out in a solvent. As the solvent, the ethers and aromatic hydrocarbons mentioned hereinbefore can be employed. When the hydroxyimino compound (VII) or salt or ester thereof is dissolved in such a solvent and a solution of the diazoalkane is added thereto, the reaction begins to proceed. The diazoalkane is used in a proportion of about 1 to 10 moles, preferably about 1 to 5 moles, per mole of the compound (VII) or salt or ester thereof. The reaction is carried out at a comparatively low temperature, generally at about −50° C. to about 20° C. and preferably about −30° C. to about 0° C. The reaction time is about 1 minute to 5 hours and preferably about 10 minutes to 1 hour.

(4) Where a dialkyl sulfate is used:

The reaction is generally conducted in water or a mixture of a water-miscible solvent with water. As such a solvent mixture, the aqueous solvents mentioned for Production Process (2) can be employed. This reaction is generally carried out in the presence of an inorganic base, such as alkali metal hydroxides, e.g. sodium hydroxide, potassium hydroxide and so on. The dialkyl sulfate is used in a proportion of about 0.5 to 10 moles, preferably about 1 to 2 moles, per mole of the compound (VII) or salt or ester thereof. The reaction temperature is about 20° to 100° C. and preferably about 50° to 100° C. The reaction time is about 10 minutes to 5 hours and preferably about 30 minutes to 3 hours.

After the above reaction, if desired, the elimination of protective group or groups and the isolation and purification of the reaction product are carried out in the same manner as Production Process 1 to give the desired cephem compound (I) or salt or ester thereof of the invention.

Where the cephem compound (I) obtained in the Production Processes 1 to 3 is a carboxylate or a free base, it can be converted to a pharmaceutically acceptable salt or ester in the routine manner, and where the cephem compound is a salt or ester, it can be converted to the carboxylate or free base also by the routine procedure. These conversions can be carried out before or after the above-described removal of the protective group.

In the aforementioned Production Processes 1 through 3, there are cases in which the cephem compound (I) or a salt or ester thereof (syn-[Z]-isomer) is produced as a mixture with the anti-[E]-isomer. From this mixture, the desired syn-isomer (that is the cephem compound (I) or salt or ester thereof) can be separated by a procedure known per se or a procedure analogous thereto. As examples of such procedure, there can be mentioned the fractionation method utilizing a difference in solubility or crystallizability or a chromatographic procedure.

The starting compound (II) or salt or ester thereof, which is used in Production Processes 1 and 2, can be produced, for example by the process described in The Journal of Antibiotics 36, 1020 (1983) and 37, 557 (1984) or a suitable process analogous thereto. The compound (III) can be produced by the process described hereinafter as a reference example, the process described in Tetrahedron 23, 387 (1967) or an appropriate process analogous thereto. The compound (V) or salt or ester thereof can be produced, for example, by reacting a compound of the general formula:

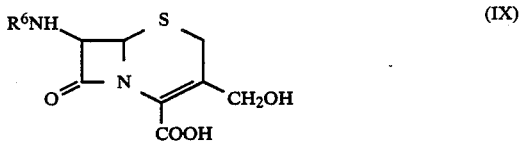

(IX)

wherein $R^6$ is an amino-protecting group such as those mentioned hereinbefore in $R^2$ and $R^4$, or a salt or ester thereof with the compound (III) or salt thereof and removing the amino-protecting group. Specifically, the reaction between the compound (IX) or salt or ester thereof and the compound (III) or salt thereof can be accomplished, for example, in the same manner as the aforesaid reaction between the compound (II) or salt or ester thereof and the compound (III) or salt thereof. After this reaction, the amino-protecting group is eliminated in the same manner as described hereinbefore and, if necessary, conversion to a salt or ester is carried out in the per se conventional manner to give the compound (V) or salt or ester thereof. As the salt and ester of compound (IX), the similar salt and ester as mentioned in the compound (II) can be employed, respectively. The compound (VI) can be produced, for example, by the process described in British Patent No. 2094794 or an appropriate process analogous thereto.

The cephem compound (I) or salt or ester thereof of the invention has a broad antibacterial spectrum and can be used in the prevention and treatment of various diseases caused by pathogenic bacteria in man and animals, such as respiratory tract and urinary tract infections. The antibacterial spectrum of the cephem compound (I) and salt or ester thereof has the following characteristics.

(1) Exceedingly high activity against a large variety of gram-negative bacteria
(2) High activity against gram-positive bacteria (for example, *Staphylococcus aureus*, *Corynebacterium diphtheriae*, etc.)
(3) Marked activity against methicillin-resistant strains of *Staphylococcus aureus*
(4) High activity against Pseudomonus species; marked inhibitory effect on pseudomonal bacteria not susceptible to the conventional cephem antibiotics.
(5) Marked activity against high β-lactamase-producing clinically isolated strains of *Citrobacter freundii* and *Enterobacter cloacae*.

To cope with pseudomonal bacterial including *P. aeruginosa*, it is common practice to use aminoglycoside antibiotics such as amikacin, gentamicin and so on. The cephem compound (I) or salt or ester thereof is as active as these aminoglycosides and yet is by far less toxic to man and animals, thus endowing a major advantage.

EXPERIMENTAL EXAMPLE 1

The MIC (μg/ml) values of the objective compounds (I) prepared in the Examples below were determined by the procedure described below. The results are set forth elsewhere in the table.

Method

The MIC of each test compound (the compounds obtained in Examples 1 and 2) was determined by the agar dilution method. Thus, 1.0 ml aliquots of serial dilutions of the test compound in water were poured into petri dishes, and 9.0 ml of Trypticase soy agar is added to each dish and stirred. A suspension (about $10^8$ CFU/ml) of each test organism is smeared on each agar plate, which is then incubated at 37° C. overnight. The lowest concentration of the test compound which causes a complete growth inhibition of the test organism was determined and taken as the MIC (minimal inhibitory concentration) against the same organism.

Test organisms (1) *Staphylococcus aureus* 308 A-1
(2) *Staphylococcus aureus* 1840
(3) *Proteus morganii* IFO 3168
(4) *Pseudomonas aeruginosa* P 9

Results

| | Test compound | (μg/ml) |
| Test organism | Compound of Example 1 | Compound of Example 2 |
| --- | --- | --- |
| (1) | 0.39 | 0.39 |
| (2) | 0.78 | 0.78 |
| (3) | 0.2 | 0.39 |
| (4) | 0.39 | 0.78 |

It is apparent from the above results that the cephem compound (I) and its salt or ester exhibit a well-balanced antibacterial action on representative strains of pathogenic bacteria which are clinically important.

EXPERIMENTAL EXAMPLE 2

Employing the compound (I) prepared in Example 1 mentioned below, the concentration levels in plasma (plasma levels of said compound) upon rectal administration were measured by the procedure described below. The results are shown in the following table.

Method

Suppositories containing the product of Example 1 which were prepared according to Example 3 mentioned below were given (50 mg/kg in terms of said product) into the rectum of three male rats No. 1 to 3 (Wistar, body weight of 300 to 400 g) being fasted for 20 hours. The anuses were closed with an adhesive agent, and blood sample were taken from the tail veins after 0.5, 1, 2 and 4 hours to determine quantitatively the plasma levels of the product of Example 1 by means of the biological assay method. As the test microorganisms for the assay, *Escherichia coli* NIHJ and *Proteus rettgeri* ATCC 9250 were employed.

Result

| Rat No. | Concentration levels in plasma (μg/ml) Time(hr) | | | |
|---|---|---|---|---|
| | 0.5 | 1 | 2 | 4 |
| 1 | 0.13 | 0.74 | 1.7 | 4.3 |
| 2 | 2.4 | 4.2 | 4.6 | 2.8 |
| 3 | 5.7 | 5.9 | 2.7 | NT |

NT: Not Tested

As is apparent from the above table, the compound (I) or a salt or ester thereof according to this invention is greatly absorbed from rectum, when is administered in the form of a suppository.

The following reference and working examples are further illustrative of the invention. It should be understood, however, that the invention is by no means limited to these examples.

In the following reference and working examples, elution from the chromatographic column was invariably carried out under TLC (thin-layer chromatography) monitoring. For TLC monitoring, Merck's 60F$_{254}$ was used as the TLC plate and the solvent used as an eluent in column chromatography was used as the developer. For detection, a UV detector was employed. The silica gel used as the column solid phase was Merck's Xieselgel 60 (230–400 mesh). The sephadex used was the product of Pharmacia Fine Chemicals. The XAD-II resin was the product of Rohm & Haas Co. The NMR spectrum was determined with the XL-100A (100 MHz), EM360 (60 MHz), EM390 (90 MHz) or T$_{60}$ (60 MHz) spectrometer, using tetramethylsilane as the internal or external standard. All the δ values shown are in ppm. The parenthesized figure for the solvent mixture is the volume ratio of component solvents. The codes used in the reference and working examples have the following meanings.

s: singlet
d: doublet
t: triplet
q: quartet
ABq: AB quartet
dd: double doublet
m: multiplet
br.: broad
J: coupling constant

REFERENCE EXAMPLE 1

To 100 ml of dichloromethane were added 1.08 g of 2-(5-amino-1,2,4-thiadiazol-3-yl)-(Z)-2-ethoxyiminoacetic acid, 1.03 g of dicyclohexylcarbodiimide and 0.765 g of 1-hydroxybenzotriazole monohydrate and the mixture was stirred at room temperature for 2 hours, at the end of which time the crystals formed were recovered by filtration. On the other hand, 1.26 g of sodium 7β-amino-3-hydroxymethyl-3-cephem-4-carboxylate was suspended in 25 ml of N,N-dimethylacetamide, and the whole crop of the above crystals was added to the suspension and the mixture was stirred at room temperature for 4 hours and, then, at 5° C. for 14 hours. The reaction mixture was shaken with 30 ml of water and 100 ml of ethyl acetate and the aqueous layer was separated. This layer was concentrated under reduced pressure to about 10 ml and the concentrate was subjected to silica gel (170 g) column chromatography. After the column was washed with acetonitrile, elution was carried out with acetonitrile-water (4:1) and the eluate as concentrated under reduced pressure to 20 ml. This concentrate was then subjected to XAD-II (200 ml) column chromatography. After the column was rinsed with water, elution was carried out with 10% (v/v) ethanol. The eluate was concentrated under reduced pressure and lyophilized. The above procedure gave 1.29 g colorless powders of sodium 7β-[2-(5-amino-1,2,4-thiadiazol-3-yl)-(Z)-2-ethoxyiminoacetamide]-3-hydroxymethyl-3-cephem-4-carboxylate.

IR(KBr)Cm$^{-1}$: 3300, 1760, 1670, 1610.
NMR(d$_6$-DMSO)δ: 1.26 (3H, t, J=7 Hz), 3.96 (2H, ABq, J=12 Hz), 4.16 (2H, q, J=7 Hz), 4.92 (1H, d, J=5 Hz), 5.60 (1H, dd, J=5.8 Hz).

Elemental analysis: as C$_{14}$H$_{15}$N$_6$NaO$_6$S$_2$.2H$_2$O
Calcd. (%): C, 34.57; H, 3.94; N, 17.28. Found (%): C, 34.76; H, 3.84; N, 17.18.

In the same manner as above, the following compound was obtained.

Sodium 7δ-[2-(5-amino-1,2,4-thiadiazol-3-yl)-(Z)-2-methoxyiminoacetamido]-3-hydroxymethyl-3-cephem-4-carboxylate IR(KBr)cm$^{-1}$: 1760, 1665, 1600.
NMR(D$_2$O)δ: 4.18 (3H, s), 4.37 (2H, s), 5.30 (1H, d, J=5 Hz), 5.92 (1H, d).

Elemental analysis: as C$_{13}$H$_{13}$N$_6$NaO$_6$S$_2$.2H$_2$O
Calcd. (%): C, 33.05; H, 3.63; N, 17.79. Found (%): C, 33.09; H, 3.55; N, 17.61.

REFERENCE EXAMPLE 2

A 300 ml stainless steel reaction column was charged with 9.21 g of 6-chloroimidazo[1,2-b]pyridazine and 150 ml of concentrated aqueous ammonia and, after closure of the reactor, the reaction was conducted at 180° C. for 8 hours. The reaction mixture was then cooled with ice-water and the resulting crystals were recovered by filtration, rinsed with water and dried to give 4.88 g of crude crystals. The whole crop of these crystals was recrystallized from 40 ml of ethanol. The procedure gave 3.25 g light yellowish brown crystals of 6-aminoimidazo[1,2-b]pyridazine melting at 198.5°–201.5° C.

NMR(d$_6$-DMSO)δ: 6.27 (2H, br. s), 6.64 (1H, d, J=10 Hz), 7.41 (1H, s), 7.72 (1H, d, J=10 Hz), 7.74 (1H, s).

EXAMPLE 1

7β-[2-(5-amino-1,2,4-thiadiazol-3-yl)-(Z)-2-methoxyiminoacetamide]-3-[(6-aminoimidazo[1,2-b]pyridazinium-1-yl)methyl]-3-cephem-4-carboxylate

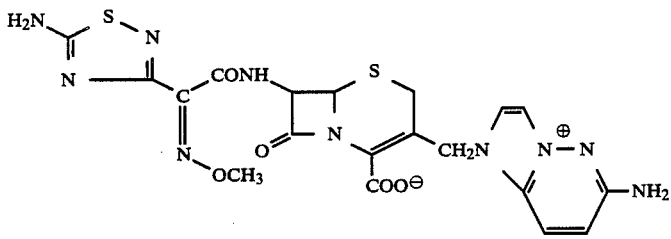

In 80 ml of dry N,N-dimethylformamide were dissolved 4.36 g of sodium 7β-[2-(5-amino-1,2,4-thiadiazol-3-yl)-(Z)-2-methoxyiminoacetamido]-3-hydroxymethyl-3-cephem-4-carboxylate and 2.68 g of 6-aminoimidazo[1,2-b]pyridazine, and under stirring and ice-cooling, 6.00 g of ethyl o-phenylenephosphate was added dropwise. The mixture was stirred under ice-cooling for 2 hours, after which the reaction mixture was subjected to silica gel (300 g) column chromatography. After the column was washed with acetonitrile and acetonitrile-water (7:1), elution was carried out with acetonitrile-water (4:1) and the eluate was concentrated under reduced pressure and lyophilized to give 3.07 g of pale yellow powders. The whole crop of powders was dissolved in N,N-dimethylformamide and subjected again to silica gel (300 g) column chromatography. The column was washed and elution carried out in the same manner as above. The fractions rich in the desired compound are pooled and concentrated under reduced pressure and the concentrate was subjected to XAD-II (300 ml) column chromatography. After the column was washed with water and 5% (v/v) ethanol, elution was carried out with 10% (v/v) ethanol. The eluate was concentrated to about one-half of the initial volume and filtered and the filtrate was concentrated again to about 50 ml. The resulting crystals were recovered by filtration, rinsed with water and dried over diphosphorus pentachloride under reduced pressure for 30 minutes to give 1.10 g of colorless crystals of the title compound.

IR(KBr)cm$^{-1}$: 1765, 1605, 1520, 1500.

NMR(D$_2$O+DCl)δ: 3.63 (2H, ABq, J=18 Hz), 4.26 (3H, s), 5.46 (1H, d, J=5 Hz), 5.56 (2H, ABq, J=15 Hz), 6.02 (1H, d, J=5 Hz), 7.47 (1H, d, J=10 Hz), 8.10 (2H, s), 8.35 (1H, d, J=10 Hz).

Elemental analysis: as C$_{19}$H$_{18}$N$_{10}$O$_5$S$_2$.7H$_2$O. Calcd. (%): C, 34.75; H, 4.91; N, 21.33. Found (%): C, 34.62; H, 4.71; N, 21.06.

EXAMPLE 2.

7β-[2-(5-amino-1,2,4-thiadiazol-3-yl)-(Z)-2-ethoxyiminoacetamido]-3-[(6-aminoimidazo[1,2-b]pyridazinium-1-yl)methyl]-3-cephem-4-carboxylate

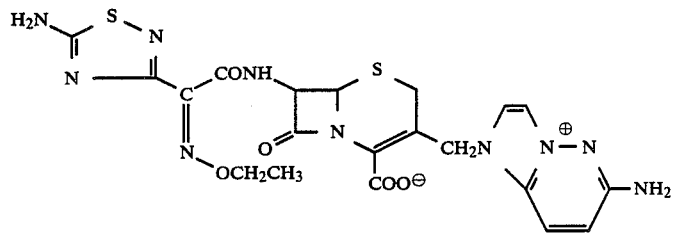

In 10 ml of dry N,N-dimethylformamide were dissolved 450 mg of sodium 7β-[2-(5-amino-1,2,4-thiadiazol-3-yl)-(Z)-2-ethoxyiminoacetamido]-3-hydroxymethyl-3-cephem-4-carboxylate and 268 mg of 6-aminoimidazo[1,2-b]pyridazine, and under ice-cooling and stirring, 600 mg of ethyl o-phenylenephosphate was added. The mixture was stirred under ice-cooling for 2 hours, after which the reaction mixture was subjected to silica gel (80 g) column chromatography. After the column was washed with acetonitrile and acetonitrile-water (7:1), elution was carried out with acetonitrile-water (5:1). The eluate was concentrated under reduced pressure and the concentrate was subjected to XAD-II (100 ml) column chromatography. The column was rinsed with water and elution was carried out with 10% (v/v) ethanol. The eluate was concentrated under reduced pressure and lyophilized to give 211 mg colorless powders of the title compound.

IR(KBr)cm$^{-1}$: 1770, 1665, 1610, 1525, 1510.

NMR(d$_6$-DMSO+D$_2$O)δ: 1.37 (3H, t, J=7 Hz), 3.41 (2H, ABq, J=18 Hz), 4.38 (2H, q, J=7 Hz), 5.25 (1H, d, J=5 Hz), 5.34 (2H, s), 5.90 (1H, d, J=5 Hz), 7.37 (1H, d, J=10 Hz), 8.10 (2H, s), 8.39 (1H, d, J=10 Hz).

EXAMPLE 3

A 250 mg portion of finely divided 7β-[2-(5-amino-1,2,4-thiadiazol-3-yl)-(Z)-2-methoxyiminoacetamido]-3-[(6-aminoimidazo[1,2-b]pyridazinium-1-yl)methyl]-3-cephem-4-carboxylate and 4750 mg of Isocacao MO-5 (produced by Kao, Ltd. in Japan) were uniformly sitrred at 40° to 45° C. and cooled to 35° C. under stirring, followed by filling the mixture into a suppository container made of plastics and gradually cooling to obtain a suppository.

What we claim is:

1. A cephem compound of the formula:

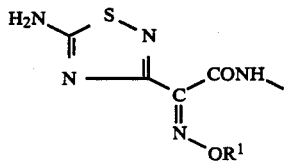

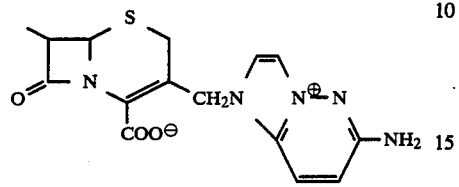

wherein R¹ is a lower alkyl group, or a pharmaceutically acceptable salt or ester thereof.

2. A compound as claimed in claim 1, wherein the lower alkyl group is a branched or straight-chain alkyl group.

3. A compound as claimed in claim 2, wherein the branched or straight-chain alkyl group is methyl, ethyl, n-propyl, i-propyl, n-butyl, i-butyl, sec-butyl or t-butyl.

4. A compound as claimed in claim 1, wherein the lower alkyl group is methyl or ethyl.

5. A compound as claimed in claim 1, which is 7β-[2-(5-amino-1,2,4-thiadiazol-3-yl)-(Z)-2-methoxyiminoacetamido]-3-[(6-aminoimidazo[1,2-b]pyridazinium-1-yl)methyl]-3-cephem-4-carboxylate.

6. A compound as claimed in claim 1, which is 7β-[2-(5-amino-1,2,4-thiadiazol-3-yl)-(Z)-2-ethoxyiminoacetamido]-3-[(6-aminoimidazo[1,2-b]pyridazinium-1-yl)methyl]-3-cephem-4-carboxylate.

7. An antimicrobial composition which contains an effective dose of a cephem compound of the general formula:

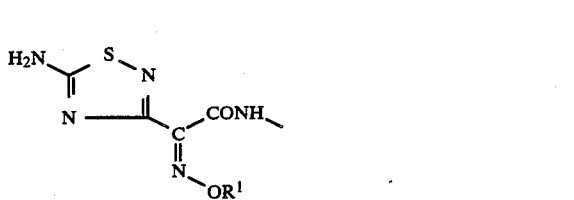

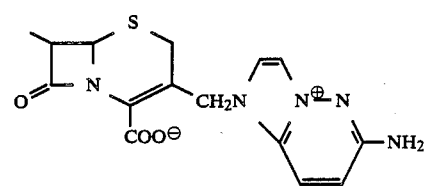

wherein R¹ is a lower alkyl group, or a pharmaceutically acceptable salt or ester thereof, together with a carrier or carriers.

8. An antimicrobial composition as claimed in claim 7, which is a composition for rectal administration.

* * * * *